United States Patent [19]

Yoshida et al.

[11] 4,168,207

[45] Sep. 18, 1979

[54] TBG ASSAY

[75] Inventors: Robert A. Yoshida, Mountain View; Joel E. Lavine, Encinitas, both of Calif.

[73] Assignee: Syva Company, Palo Alto, Calif.

[21] Appl. No.: 821,385

[22] Filed: Aug. 3, 1977

[51] Int. Cl.$^2$ ............................................. G01N 31/14
[52] U.S. Cl. ......................................... 435/7; 23/915; 435/26
[58] Field of Search ................. 195/103.5 A, 103.5 R, 195/63; 424/12

[56] References Cited

U.S. PATENT DOCUMENTS

| | | | |
|---|---|---|---|
| 3,817,837 | 6/1974 | Rubenstein et al. | 195/103.5 A |
| 4,040,907 | 8/1977 | Ullman et al. | 195/103.5 R |
| 4,043,872 | 8/1977 | Blakemore et al. | 195/103.5 A |

OTHER PUBLICATIONS

Levy et al., J. Clin. Endocrinol. Metab., 35:565, 1972.

*Primary Examiner*—Thomas G. Wiseman
*Attorney, Agent, or Firm*—Bertram I. Rowland

[57] ABSTRACT

Method and compositions are provided for determining the thyroxine binding capacity of serum, the value finding use in determinations of free thyroxine index. A competitive assay is performed where antibody for T-3 (anti-triiodothyronine) and serum thyroxine binding sites compete for T-3(triiodothyronine) in the assay medium: the T-3 is present as free T-3 added in a predetermined amount and T-3 conjugated to an enzyme. By combining the materials in a buffered aqueous medium with enzyme substrates, and determining the rate of reaction by the changing concentration of a light absorptive substance over a predetermined period of time, the thyroxine binding capacity of the serum can be determined.

5 Claims, No Drawings

TBG ASSAY

BACKGROUND OF THE INVENTION

1. Field of the Invention

The measurement of available thyroxine binding sites in serum is important in thyroid function screening tests, due to the innate relationship of the available thyroxine binding sites and the total thyroxine concentration to the concentration of free or unbound thyroxine. Thyroxine is normally almost completely bound in serum to carrier proteins. Roughly 70% is normally bound to TBG, 20% to thyroid binding prealbumin and 10% to albumin. The free thyroxine concentration in serum shows excellent correlation with, and is thought to be the true determinant of the thyroid status of the individual. The concentration of free thyroxine (T-4) in serum is very small and cannot be accurately or easily measured, the free T-4 being estimated as about 35 pg/ml. Therefore, one utilizes the relationship where free T-4 is proportional to the bound T-4 concentration divided by the free binding site concentration.

2. Brief Description of the Prior Art

Numerous techniques are presently available for determining thyroxine binding capacity. These techniques include Reverse-flow Electrophoresis, Robbins, Arch. Biochem. 73:461, 1956; Dextran-coated Charcoal, Roberts and Nikolai, Clin. Chem. 15:1132, 1969; Ion-exchange Resin, Roberts and Nikolai, Ibid.; Radioimmunoassay, Hamad, et al, J. Clin. Endocrinol. Metab. 31:166, 1970 and Competitive Ligand-binding Assay, Levy, et al, Ibid. 35:565, 1972.

SUMMARY OF THE INVENTION

Method and compositions are provided for determining thyroxine binding capacity in serum. A serum sample is combined with anti(triiodothyronine) and triiodothyronine (T-3), both free and conjugated to an enzyme in an aqueous medium. The enzyme rate is then determined over a predetermined period of time by adding the appropriate enzyme substrates and following the rate of the reaction. By comparison to a known standard, the binding capacity of the serum can be determined.

DESCRIPTION OF THE SPECIFIC EMBODIMENTS

A simple accurate and rapid method is provided for quantitatively determining the thyroxine binding capacity of a serum sample. The method involves a plurality of equilibria where a single determined value is definitive as to the amount of binding capacity for thyroxine in the serum.

In carrying out the subject method, a buffered aqueous medium is employed into which is introduced the serum sample, antibodies to T-3(anti(T-3)), T-3, an enzyme-bound-T-3, particularly an oxidoreductase requiring NAD or NADP, more particularly the enzyme malate dehydrogenase, preferably heart malate dehydrogenase, e.g. pig heart or beef heart, and the enzyme substrates. The reagents are added, and the enzymatic activity determined. The enzymatic activity or rate is indicative of the amount of thyroxine binding capability in the serum.

The method employs two sources of binding capacity and two sources of T-3. The two sources capable of binding T-3 are serum binding proteins, primarily thyroxine binding globulin, and anti(T-3). These two sources compete for the limited amount of T-3 present in the serum. Anti(T-3) which is not bound to T-3 in solution can then bind to the T-3 which is conjugated to the enzyme. Binding of anti(T-3) to the T-3 conjugated to the enzyme will result in a reduced activity of the enzyme and therefore a reduced amount of NAD transformed to NADH during the time interval of the measurement. By comparing the rate of the unknown sample to the rates of serum calibrators having known levels of T-3 uptake, the relative T-3 uptake of the sample can be determined. By determining the ratio of the sample T-3 uptake and normal serum pool T-3 uptake and multiplying this by the total concentration of thyroxine (T-4) present in the serum, one obtains the free thyroxine index (FTI) which is indicative of the amount of free thyroxine in the medium.

The method permits the use of extremely small samples of serum. Usually, less than 50 $\mu$l is required, preferably less than 30 $\mu$l, and usually more than about 10 $\mu$l will be employed. Therefore, a small amount of serum can be used for this test as well as many other tests, so as to provide minimum discomfort to the patient.

The solution will be buffered in the range of 5 to 10, more usually 6 to 9.5, preferably 7 to 9.5 and more preferably 8 to about 9.5. Various buffers may be used such as tris, barbital, phosphate, glycine, and the like. The preferred buffers are tris-malate and glycine. The concentration of buffer will generally be in the range of about 0.01 to 1, more usually from about 0.1 to 0.4 M.

Other additives may also be present in the assay medium, which are employed for preserving or protecting individual reagents or for aiding the performance characteristics of the assay. Particularly, protein may be included in the assay medium, usually gelatin, which will generally be present in amounts of about 0.1 to 1 weight percent, more usually from about 0.05 to 0.5 weight percent. Other additives include ethylenediaminotetraacetic acid in amounts of from about 0.005 to 0.1 weight percent, more usually from about 0.01 weight percent.

The amount of T-3 which is employed in the assay medium is relatively critical, since it must be great enough to swamp any endogenous T-3 in the serum and yet allow for a distribution between the thyroxine binding capacity and the anti(T-3) which ultimately allows for a satisfactory range of enzyme activity over the thyroxine binding capacity of interest. That is, there must be enough T-3 to bind to the TBG present in the serum while having a sufficient amount of remaining T-3 to bind to a portion of the anti(T-3), so as to leave some anti(T-3) to bind to the T-3 which is conjugated to the enzyme. The amount of T-3 will generally be in the range of about 0.25 to 5 ng/ml, more usually from about 0.5 to 2 ng/ml and preferably from about 1 to 1.5 ng/ml. As the enzyme-bound-T-3, malate dehydrogenase can be employed having on the average about 1.5 to 7, more usually from about 2 to 6 T-3s per enzyme. The percent of the original activity of the enzyme after conjugation will generally range from about 25 to 90, more usually from about 40 to 75 percent. Upon saturation binding with anti(T-3) the inhibition or the percent reduction in activity of the conjugated enzyme will generally range from about 20 to 80, more usually from about 25 to 60 percent.

For the most part, the malate dehydrogenase-bound-T-3 will have the following formula:

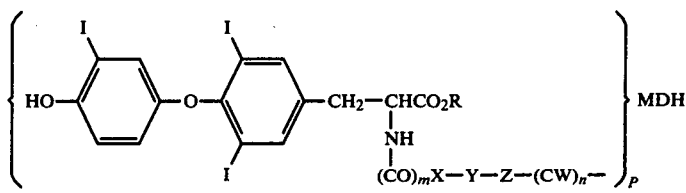

wherein:
- MDH is malate dehydrogenase, particularly heart malate dehydrogenase, and more particularly pig heart malate dehydrogenase;
- R is hydrogen or alkyl of from 1 to 3 carbon atoms, particularly methyl;
- m and n are integers of from 0 to 1, preferably 1;
- W is oxygen or imino, particularly oxygen;
- Y is a bond, oxy, alkylimino of from 1 to 3 carbon atoms, preferably methylimino, or amido (—CONH—);
- X and Z are alkylene or alkenylene i.e. 0–1 site of ethylene unsaturation, either straight chain or branched, preferably straight chain, of from 1 to 4 carbon atoms, more usually of from 1 to 2 carbon atoms, particularly methylene or polymethylene; and
- P is on the average at least 1 and not more than 20, usually 2 to 12, preferably 2 to 8.

Illustrative groups include methylene carbonyl, crotonyl-4-yl, di(carbonylmethylene)oxy, N-di(carbonylmethylene) methylimino, succindioyl, glutardioyl, maledioyl, etc.

The amount of enzyme which is employed will vary widely and will be chosen to provide a desired enzymatic rate in the assay medium over the range of binding capacity of interest. Generally, for a spectrophotometric measurement one would observe a change in mOD at 340 nm at 30° C. of from about 150 to 1000 during the predetermined time interval measured, more usually from about 250 to 600 mOD.

The amount of anti(T-3) which is employed will also vary widely and will be matched with the amount of enzyme. Desirably, the amount of anti(T-3) will be matched with the enzyme to provide the change in mOD indicated above. The ratio of antibody and enzyme can be readily determined empirically by employing serum having thyroxine binding capacity of known degree as determined by alternative techniques. Usually, the ratio of antibody based on binding sites to T-3 conjugated to enzyme will be in the range of about 0.01 to 100 per conjugated T-3.

Large excesses of enzyme substrate will be employed to insure that the substrate is not rate limiting. The concentration of NAD in the assay medium will generally be in the range of about 0.001 to 0.05 M, more usually from about 0.005 to about 0.02 M. The amount of malate will generally be from about 10 to 100 mM. Conveniently, the various acidic materials are present as their sodium salts.

In performing the assay various protocols may be employed. Two or more reagents may be combined, with various incubation times between additions of additional reagents. Normally, the total complement of substrates, including cofactors, for the enzyme will not be combined with the enzyme until all of the other reagents are present in the assay medium.

Conveniently, the enzyme-bound-T-3 is dissolved in an appropriate buffer solution and combined with a predetermined amount of T-3 and the serum sample. The mixture may be incubated at a temperature in the range of 15° to 40° C. for from about 1 to 30 minutes, usually 2 to 10 minutes to allow the T-3 to bind to available TBG binding sites.

Alternatively, the serum sample, enzyme-bound-T-3, T-3, and enzyme substrates may be combined substantially simultaneously, antibody and co-factor being added at the last as a single reagent.

After combining all the materials, the NADH absorption will be rapidly read. Usually, less than 5 min., more usually less than 1 min. and generally greater than about 5 sec. will be required to allow for equilibration the medium. The medium is then maintained at a constant temperature, generally in the range of about 25° to 40°, preferably in the range of about 30° to 40° and more preferably at about 37° C. The change in NADH absorption may be followed over a wide variation of time intervals, but the intervals will generally be at least about 30 sec and not more than about 6 hrs., preferably from about 1 min. to 1 hr., and more preferably about 30 min. As indicated previously, the absorption will be read at 340 nm, which is close to the absorption maximum of NADH in the assay medium. Any other wavelength could be chosen which is sensitive to changes in NADH concentration in the medium.

By carrying out a series of determinations with serum having known thyroxine binding capacity, as determined by alternative techniques or once the subject technique is standardized, the subject technique, a curve can be obtained relating to change in absorption with thyroxine binding capacity.

EXPERIMENTAL

The following examples are offered by way of illustration and not by way of limitation.

All temperatures not otherwise indicated are centigrade. All parts or percents not otherwise indicated are by weight, except where two liquids are mixed and are then by volume. The following abbreviations are employed: DMF-dimethylformamide, THF-tetrahydrofuran: AcOH-acetic acid; TLC-thin layer chromatography

EXAMPLE 1

Preparation of malate dehydrogenase-bound-T-3

Following is an exemplary preparation of the titled compound.

A. The reaction was carried out in a 25 ml round bottom flask wrapped in foil, equipped for magnetic stirring and placed under an argon atmosphere. A solution of 0.591 g T$_3$-methyl ester hydrochloride was formed in a solvent system consisting of 2 ml DMF and 2 ml THF. To this solution was added 146 µl of triethylamine (1.25 eq) and the solution stirred for fifteen minutes. Then 0.130 g (1.20 eq) of N-methyliminodiacetic acid anhydride (MEMIDA anhydride) was added in a single portion. When TLC on $SiO_2$ showed complete reaction, the solvent system for TLC analysis was $AcOH/MeOH/CHCl_3$: 5:10:85.), the solvent was removed on a Buchi rotoevaporator initially using a water aspirator and finally a mechanical vacuum pump. The water bath temperature was not allowed to exceed 30°. The residue was dissolved in 8.5 ml dry THF. To the solution was added 76 ml of ethyl acetate and the mixture vigorously shaken. The resulting suspension was gravity filtered and the filtrate washed in a separatory funnel with 10 ml water, then 20 ml water, then $2 \times 15$ ml of a saturated salt solution to dry the solution. Further drying was effected with $MgSO_4$ which was then removed by gravity filtration. The solvent was removed on the evaporator and the product residue suspended in $CHCl_3$. Petroleum ether was then added as cosolvent in the suspension. The solvent was then removed by filtration and the solid product was dried in a desiccator under vacuum. After drying in the desiccator, 0.346 g of a white powder of T-3 MEMIDA was obtained.

B. A solution of 8.44 mg (10.6 μmol) of $T_3$-MEMIDA in 300 μl of dry THF was prepared in a 5 ml pear shaped flask wrapped in foil and equipped for magnetic stirring. Using 1 ml volumetric flasks, a solution of 26.6 mg N-hydroxysuccinimide (NHS) (0.231M) in 1 ml THF and a solution of 46.0 mg dicyclohexylcarbodiimide(DCC) (0.223 M) in 1 ml THF were prepared. To the reaction flask containing the $T_3$-MEMIDA was added 48 μl (11.1 μmol) of the NHS solution. The reaction mixture was then cooled by placing the reaction flask in an ice-water bath for 20 minutes. To the cooled mixture was added 50 μl (11.1 μmol) of the DCC solution. The reaction mixture was kept at ice bath temperature for one hour and then brought to room temperature and left overnight. Large crystals of dicyclohexylurea were present in the reaction flask. The solution was filtered through a glass wool plug in a capillary pipet to remove the urea. The solvent was then removed by Büchi rotoevaporator. The material in the flask was taken up in 0.2 ml of a 20% n-hexane/$CH_2Cl_2$ solution and chromatographed on a cellulose column with 20% n-hexane/$CH_2Cl_2$ as the eluant. The column was prepared in a $0.5 \times 14.4$ cm capillary pipet. The size of the fractions was approximately 0.5 ml and the fractions were analyzed by TLC on cellulose. Ester containing fractions were combined and the solvent was removed on a Büchi rotoevaporator. The NHS ester was dissolved in 250 μl of diglyme. The diglyme solution (5 μl) was dissolved in 1 ml of 0.1 N NaOh and the uv spectrum of the solution obtained. The absorbance at 312 nm was used to estimate the concentration of the NHS ester. The value of $4.25 \times 10^3$ was used as the extinction coefficient. The yield was 60.2%.

C. The enzyme to be conjugated, MDH (from pig heart), was centrifuged out of an ammonium sulfate suspension, the supernatant was removed, and the enzyme was resuspended in 50 mM $NaHCO_3$-$Na_2CO_3$ (pH 9.0-9.1). The enzyme was exhaustively dialyzed against the same 50 mM carbonate buffer. The buffer was then used to adjust the volume of the enzyme solution to give a concentration of 9-10 mg/ml MDH. The extinction coefficient used for MDH (pig heart) was $E_{1\%}$ 280 nm = 2.94.

D. A 2.7 ml aliquot of a 9.61 mg/ml MDH (from pig heart) solution in 50 mM $NaHCO_3$-$Na_2CO_3$ buffer (pH 9.04) was added to a 5 ml Pierce Reacti-vial ™ which was equipped for magnetic stirring and maintained in an ice-water bath. Using a 250 μl Hamilton syringe, 0.9 ml of carbitol was added to the enzyme preparation at a rate of 25 μl/min. Fairly vigorous magnetic stirring was maintained during the addition of the carbitol and later during addition of the T-3 MEMIDA. In a single portion, 63 μl of a diglyme solution containing the purified NHS ester of $T_3$-MEMIDA ($2.16 \times 10^{-2}$ M) was added by syringe. Twenty minutes was allowed for completion of the reaction. Then the reaction mixture was assayed to determine the extent of inactivation of the enzyme and the magnitude of the inhibition by anti-$T_3$. An aliquot of the reaction mixture (1.2 ml) was removed and dialyzed against 0.5 M $KH_2PO_4$ (pH 7.0). A second aliquot of the NHS ester solution (6 μl) was added with microcaps. Again 20 minutes were allowed for the reaction to go to completion before assaying. Again, 1.2 ml of the reaction mixture was removed and dialyzed against 0.50 M $KH_2PO_4$ (pH 7.0). Finally, 2 μl of the NHS solution was added to the remainder of the reaction mixture in the Reactivial. After 20 min. the mixture was assayed, then dialyzed against 0.50 M $KH_2PO_4$ (pH 7.0).

E. Sephadex G-50 was prepared by overnight swelling in 0.50 M $KH_2PO_4$ (pH 7.0) at 2°-4°. A $0.9 \times 100$ cm column of this material was prepared and conditioned by a continuous flow of 0.50 M $KH_2PO_4$ (pH 7.0) for 2 hrs. and then passage of BSA in an aqueous solution through the column. After 2 days of dialysis against 0.50 M $KH_2PO_4$ (pH 7.0), the conjugates were passed through the column. Fractions were collected with an LKB fraction collector. The appropriate fractions were pooled and concentrated at 2° in a collodion bag apparatus. Finally the volume was brought to 1.0 ml with 0.50 M $KH_2PO_4$ (pH 7.0). All of the above steps were carried out in the cold room at 2°-4°.

The conjugates were assayed for the percent of the original activity and percent inhibitability with excess antibody according to the following protocol. All enzyme assays were performed using a Bausch and Lomb Spectronic 100 equipped with a thermostatted cell holder and one cm. path length cuvettes. The cuvettes containing buffer and substrates were preincubated for at least three minutes at 30° in a constant temperature bath, prior to addition of enzyme conjugate. Typically 5 μl of the conjugate solution was diluted into 1.8 ml of the glycine assay buffer and mixed by inverting $3 \times$, then 5 μl of this dilution was added to the assay mixture. The rate used was typically the rate in the second minute of the reaction. To determine the rate in the presence of anti(T-3), 25 μl of purified antisera was added to the cuvette with the assay buffer and substrates. Initial rates were calculated from absorbance versus time plots. To each cuvette was added 1.8 ml of an aqueous solution 0.1 M glycine-NaOH, 0.1% rabbit serum albumin and 0.01% EDTA. 2Na ® (pH 9.5); 100 μl 2 M L-malic acid (pH 9.5), and 100 μl 0.2 M β-NAD, pH 5.02.

The following Table indicates the results

TABLE I

| Conjugate | Equivalents Hapten added | % original Activity | % Inhibition |
|---|---|---|---|
| 1 | 3.5 | 64.9 | 48.5 |
| 2 | 4.0 | 54.5 | 50.1 |
| 3 | 4.4 | 47.3 | 44.2 |

EXAMPLE 2

T3-diglycolic acid derivative conjugate to bovine gamma globulin (BgG)

A. To a slurry of one gram (1.54 mmol) of triiodothyronine (T3) in 50 ml of dry methanol in a 100 ml flask equipped with side-armed adaptor with a gas inlet tube and a $CaCl_2$ drying tube, flushed with argon, HCl gas was introduced at a fast rate while cooled by an ice-$H_2O$ bath. After the HCl gas was added to the solution for five minutes to saturation, the clear solution was stoppered and stirred overnight. Concentration of the mixture under reduced pressure gave a white solid which weighed 1.056 g after being dried in vacuo. The yield was quantitative. Mp. 204° dec.

B. To the suspension of 500 mg (0.715 mmol) of the above ester in 35 ml of THF (distilled over LAH) under an argon blanket was added 80 µl (~0.6 mmol) of triethylamine at room temperature. To the mixture was then added 93 mg (0.8 mmol) of diglycolic anhydride, the flask capped with a septum and stirred overnight. TLC on silica ($HOAc:MeOH:CHCl_3/1:9:90$) showed essentially complete reaction. The reaction mixture was then concentrated to dryness. The residue was extracted with 150 ml of ethyl acetate, the extract washed with saturated brine and then dried over $MgSO_4$. Concentration of the solution gave a foamy solid of crude product weighing 510 mg. Purification of this product by Sephadex LH20 (15% $CH_3OH/CH_2Cl_2$) gave an analytical sample, mp. 210°.

C. Twenty-four mg of 1-ethyl-3-(3'-dimethylaminopropyl)carbodiimide (ECDI) ($1.25 \times 10^{-4}$ moles) was added to a solution of 78.1 mg ($1 \times 10^{-4}$ moles) of the above product, 13 mg ($1.1 \times 10^{-4}$ moles) of N-hydroxy succinimide and 15 µl ($1.08 \times 10^{-4}$ moles) of triethylamine in one ml of dry THF under nitrogen at 0° (ice-$H_2O$ bath). The solution was stirred for two hours at 0°, then in the cold room overnight.

The above solution was added dropwise to a solution of 250 mg of BgG in 10 ml of pH 9.5 $Na_2CO_3$-$NaHCO_3$ buffer at 0° (ice bath). After stirring at 0° for 2 hours, the stirring was continued in the cold room for 6 more hours. The resulting mixture was dialyzed against 4 l. of pH 9.5 $NaHCO_3$-$Na_2CO_3$ buffer in the cold room for three days, then against $3 \times 4$ l. of $NH_4OH$ at pH 9. The resulting mixture was centrifuged at 10,000 rpm for 1.5 hours, then the supernatant was concentrated by a collodion bag to 3 ml and then was passed thru a Sephadex G-50 with pH 9.5 $NH_4OH$. The protein fraction was lyophilized to give 85 mg of conjugate. Hapten number, 42, was determined by uv.

The above conjugate was injected into sheep according to known procedures to obtain T-3 specific antisera. The bleeds which were obtained were treated as follows:

Fifty ml of antisera was precipitated with an equal volume of saturated ammonium sulfate at 4°. The $NH_4SO_4$ was added dropwise from a burette into the antisera which was mixed vigorously. After complete addition of saturated ammonium sulfate, the mixture sat in the cold room for one hour. The precipitate was centrifuged in the Sorvall (small rotor) at 10,000 rpm for 30 minutes at 0°. The supernatant was discarded and the precipitate was redissolved in 20 ml of 0.055 M Tris pH 8.1, 0.05% $NaN_3$. This was dialyzed for two days with four changes of 1000 ml of the same buffer. After dialysis, the total volume of the IgG fraction was measured and an aliquot was saved as a control. The remainder was treated with Rexyn Ag4 (Fisher Scientific Co.).

The Rexyn Ag4 was washed with 0.1 M Tris-HCl pH 7.4 to convert it all to the $Cl^-$ form. Twenty grams of Rexyn Ag4 was weighed out and placed on a scintered glass funnel. The resin was washed with $5 \times 40$ ml aliquots of 0.1 M Tris-HCl pH 7.4 at room temperature. The resin then sat overnight at 4° with the same buffer, was rinsed once more, dried by vacuum filtration, and stored at room temperature.

Sixteen grams of Rexyn Ag4 was added to 47.5 ml of the precipitated T3 antisera. The mixture was maintained at 4° while being mixed very slowly for four days. The Rexyn Ag4 was allowed to settle for a couple of minutes and the antisera was pipetted off the surface.

An aliquot of antisera was diluted 1:10 in assay buffer, 0.1 M glycine, pH 9.5, 0.01% EDTA, 0.1% RSA.

In performing a thyroxine binding capacity assay the following reagents are employed:

Malate dehydrogenase-bound-T-3 solution (Ex. 1)
  40% glycerol
  0.2% type B gelatin
  0.01% EDTA
  0.01% $NaN_3$
  q.a.s. water
T-3 lyophilized
  0.1% dextran T-70
Buffer solution, pH 8.3
  0.3 M glycine
  0.6 M malate
  0.01% $NaN_3$
  q.a.s. $H_2O$
Anti(T-3) lyophilized
  0.4 M NAD
  0.2% type A gelatin
  0.01% $NaN_3$
Anti(T-3) working reagent
  1:20 dilution of anti(T-3) lyophilized in:
  0.2% type A gelatin
  0.01% $NaN_3$
  0.15 M glycine
  q.a.s. water The protocol employed is as follows:

A solution is prepared of 50 µl of the enzyme solution and 500 µl of the buffer solution containing 2 ng of the T-3 reagent;

to the above solution is added 20 µl of serum, followed by the addition of 1 ml of the anti(T-3) working reagent;

the solutions are mixed and 20 secs after the addition of anti(T-3) working reagent the initial O.D is read at 37° at 340 nm in a thermostatted cuvette;

the solution is then incubated for 30 mins. at 37° and a second reading taken at 340 nm at 37°. With two series of twelve examples each, at half normal and normal TBG concentrations, the coefficients of variation were 0.91 and 1.21% respectively. This converts to 2 and 2.5% uptake respectively. In correlation studies with commercially available T-3 uptake kit methods employing isotope and absorbent tablets for separation, the correlation was 0.85.

The subject method provides a convenient, accurate and rapid technique for determining thyroxine binding globulin or thyroxine binding capacity of serum. The method is rapid and accurate with few manipulative steps, so as to minimize operator error. No separation step is required, so that there need be no concern for efficient segregation between antibody bound and unbound reagent. Furthermore, generally available equipment may be employed, since only ultraviolet readings are required. The results can be rapidly obtained avoiding long time intervals between the request for the result and the reporting of the result.

Although the foregoing invention has been described in some detail by way of illustration and example for purposes of clarity of understanding, it will be obvious that certain changes and modifications may be practiced within the scope of the appended claims.

What is claimed is:

1. A method for determining thyroxine binding capacity of a serum sample which comprises:
   (1) combining in an aqueous medium at a pH in the range of about 5 to 10 under conditions which allow triiodothyronine to bind to available thyroxine binding globulin binding sites:
   (a) said serum sample;
   (b) a predetermined amount of triiodothyronine in substantial excess over endogenous triiodothyronine and in the range of about 0.25 to 5 ng/ml in said assay medium;
   (c) anti(triiodothyronine); and
   (d) enzyme-bound-triiodothyronine wherein the activity of said enzyme-bound-triiodothyronine is diminished upon binding to anti(triiodothyronine); and
   (2) determining the enzyme activity of said enzyme-bound-triiodothyronine in said assay medium as compared to the enzyme activity determined with a serum sample having a known thyroxine binding capacity.

2. A method according to claim 1, wherein said enzyme is malate dehydrogenase and said determining is performed by introducing malate and NAD and determining the change in light absorption over a predetermined time at about 340 nm.

3. A method according to claim 2, wherein said malate dehydrogenase is heart malate dehydrogenase.

4. A method according to claim 2, wherein said serum sample is of from about 10 to 50 μl.

5. A method according to claim 2, wherein the ratio of enzyme-bound-triiodothyronine and anti(triiodothyronine) provides a change in mOD at 340 nm at about 30° C. in the range of about 250 to 600 over a period of at least about 5 minutes.

* * * * *